(12) United States Patent
Spector

(10) Patent No.: US 9,289,585 B2
(45) Date of Patent: Mar. 22, 2016

(54) COMPRESSED ARTICLES WITH MICROENCAPSULATION

(71) Applicant: Donald Spector, New York, NY (US)

(72) Inventor: Donald Spector, New York, NY (US)

( * ) Notice: Subject to any disclaimer, the term of this patent is extended or adjusted under 35 U.S.C. 154(b) by 395 days.

(21) Appl. No.: 14/064,818

(22) Filed: Oct. 28, 2013

(65) Prior Publication Data

US 2014/0048436 A1 Feb. 20, 2014

Related U.S. Application Data

(63) Continuation-in-part of application No. 11/439,831, filed on May 23, 2006.

(51) Int. Cl.
| | |
|---|---|
| *A61K 8/37* | (2006.01) |
| *A61M 35/00* | (2006.01) |
| *A61B 19/02* | (2006.01) |
| *A61M 21/02* | (2006.01) |
| *A61K 8/02* | (2006.01) |
| *A61Q 17/00* | (2006.01) |
| *A61Q 19/00* | (2006.01) |
| *A61K 8/11* | (2006.01) |
| *B08B 1/00* | (2006.01) |

(52) U.S. Cl.
CPC ............. *A61M 35/00* (2013.01); *A61B 19/02* (2013.01); *A61K 8/0208* (2013.01); *A61K 8/0212* (2013.01); *A61K 8/11* (2013.01); *A61M 21/02* (2013.01); *A61Q 17/005* (2013.01); *A61Q 19/00* (2013.01); *B08B 1/00* (2013.01)

(58) Field of Classification Search
CPC . A61K 8/0208; A61K 8/0212; A61K 8/0219; A61K 8/342; A61Q 19/10; A61Q 19/10
See application file for complete search history.

(56) References Cited

U.S. PATENT DOCUMENTS

| | | | |
|---|---|---|---|
| 2,659,935 A | 11/1953 | Hammon | |
| 2,952,462 A | 9/1960 | Planin | |
| 4,241,007 A | 12/1980 | Tanaka et al. | |
| 4,780,361 A | 10/1988 | Schlein | |
| 4,881,915 A | 11/1989 | Liaw | |
| 5,316,689 A | 5/1994 | Farrell | |
| 6,034,051 A | 3/2000 | Lindauer et al. | |
| 6,159,487 A | 12/2000 | Znaiden et al. | |
| 6,432,272 B1 | 8/2002 | Hollenberg et al. | |
| 6,900,249 B2 | 5/2005 | Mork et al. | |
| 7,122,238 B2 | 10/2006 | Macedo | |
| 7,179,772 B2 | 2/2007 | Keenan et al. | |
| 2004/0185730 A1 | 9/2004 | Lambino et al. | |
| 2005/0153862 A1 | 7/2005 | Lau et al. | |

OTHER PUBLICATIONS

Reply Brief filed on Sep. 18, 2012 in U.S. Appl. No. 11/424,152.
Appeal Brief filed on Mar. 26, 2012 in U.S. Appl. No. 11/424,152.
Response to Final Office Action filed on Dec. 6, 2011 in U.S. Appl. No. 11/424,152.
Amendment in Response to Office Action filed on Aug. 8, 2011 in U.S. Appl. No. 11/424,152.
Response to Final Office Action filed on Jul. 15, 2011 in U.S. Appl. No. 11/424,152.
Amendment in Response to Office Action filed on Feb. 17, 2011 in U.S. Appl. No. 11/424,152.
Response filed on Aug. 3, 2010 in U.S. Appl. No. 11/424,152.
Response filed on Oct. 21, 2009 in U.S. Appl. No. 11/424,152.
Response filed on Mar. 23, 2009 in U.S. Appl. No. 11/424,152.
Response to Non-Final Office Action filed on May 16, 2007 in U.S. Appl. No. 11/424,152.
Response to Non-Final Office Action filed on Feb. 4, 2008 in U.S. Appl. No. 11/424,152.

*Primary Examiner* — Kyle Purdy
(74) *Attorney, Agent, or Firm* — Collard & Roe, P.C.

(57) ABSTRACT

A compressed article of hygiene is formed by a compressed cloth that has been compressed by dehydration or vacuum pressure into a coin shape and that is expandable upon contact with a liquid, and a plurality of microencapsulated beads containing a material. The microencapsulated beads are attached and embedded in the compressed cloth. Upon contact with water, expansion of the compressed cloth is unconstrained, and the compressed cloth when expanded has a shape of a facial mask with openings for eye, nose and mouth. The material is a facial treatment material that hardens upon drying.

7 Claims, 5 Drawing Sheets

COMPRESSED ARTICLES WITH MICROENCAPSULATION

CROSS-REFERENCE TO RELATED APPLICATIONS

The present application is a continuation-in-part of U.S. patent application Ser. No. 11/439,831 filed on May 23, 2006, the disclosure of which is incorporated by reference.

BACKGROUND OF THE INVENTION

This application relates to the field of compressed paper and woven goods.

Products made in a compressed state are small, for example, the size of a coin or a button. When such products are put into a liquid, for example, water, they expand, become larger, and are then suitable for their intended purpose. For example, buttons of compressed paper can be hydrated to be used as wipes. In other examples, compressed fabrics are hydrated to make towels, face cloths, tee shirts, and other clothing. Compressed sponges that expand upon contact with water are another example.

Compressed goods are useful because their light weight and small size make shipping and handling them easier than otherwise. There is a need to provide compressed goods with enhanced features, for example, ones that provide medicinal or comfort therapies.

SUMMARY OF THE INVENTION

In one aspect of the invention, microencapsulated materials are added to compressed products. Generally, the materials are added to the products before the products are compressed. The microencapsulated products can also be added to the products after they have been compressed.

Microencapsulation permits a wide range of products to be incorporated into these dehydrated compressed products while maintaining the dry, compressed nature of the products. The coatings of microencapsulated beads of material can be soluble in various types of liquid, for example, water. Moreover, in some examples, it may be desirable that the coatings only release material upon mechanical force, e.g., friction.

Methods of making an article are provided, the methods comprising forming the article, that comprises paper or fabric, in a size of intended use; attaching a plurality of microencapsulated beads containing a material therein to the paper or fabric; and compressing the article to a compressed size that is smaller than the size of intended use. In one embodiment, the step of compressing the article comprises dehydrating the article. In another embodiment, the step of compressing the article comprises exposing the article to vacuum pressure. In yet another embodiment, the method further comprises contacting the article with a liquid to expand the article to approximately the size of intended use.

In another aspect of the invention, the articles comprise a liquid-expandable paper or fabric, and a plurality of microencapsulated beads containing a material therein attached to the paper or fabric. Generally, the paper or fabric material is in a compressed state and the material remains compressed until a liquid contacts the material. This application may refer to the compressed paper or cloth as a compressed coin. In some examples, the microencapsulated beads are attached to the surface of the paper or fabric. In other examples, the beads are embedded within the fabric or paper.

In one embodiment, the material is released from the beads upon expansion of the paper or fabric in the liquid. In some examples, the material comprises therapeutic compounds such as antibiotics or alcohols, to be used, for example, for cleaning wounds or other medicinal purposes. Articles having such materials can be useful in military or third world environments. In other examples, the material comprises comforting compounds such as a fragrance, an oil, salt, a vitamin, a skin-moisturizer, or combinations thereof. Articles having such materials can be used as compresses for aromatherapy or other relaxation therapies. In another embodiment, the materials can be in the form of a hardening facial mask. These materials can be in the form of clay, resin, or other material that is pliable when wet but hardens upon drying.

In some embodiments, articles in accordance with the present invention comprise a towel, a face cloth, or a wiping cloth. If the article is used as a facial mask, it is supplied with cut-outs for the eyes, nose and mouth.

There are many uses for the micro encapsulated products in accordance with various aspects of the present invention. One use is combining the compressed coins with coated alcohol or antibiotic. When they are expanded, they then have the ability to be able to be used to clean wounds and other medical uses. This might be of particular value in third world areas or military situations.

Another use is to microencapsulate fragrances and/or oils with these compressed coins. In this application, these coins would be placed in warm water. As they are expanded they can be used as compresses for aromatherapy or other relaxation therapies.

It is believed that there are substantial uses and a substantial business for combining these two technologies. Without the dryness of the microencapsulation it would cause the coins to expand and/or the ingredients to be dissipated.

The articles can be packaged and sold individually, or in groups. In one embodiment, a plurality of similar articles are packaged in a strip, with each coin individually sealed in the strip. Thus, a single coin could be cut off of the strip without affecting the seal of the others, so that they are not exposed to air when removing a single coin. The strip could be formed from a plastic material that can be colored or printed to indicate the contents of the strip. The strip could have perforations along the seam to make separation easier. The strip could also have a weakening line extending to the area enclosing each coin to allow tearing of the packaging along the weakening line.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
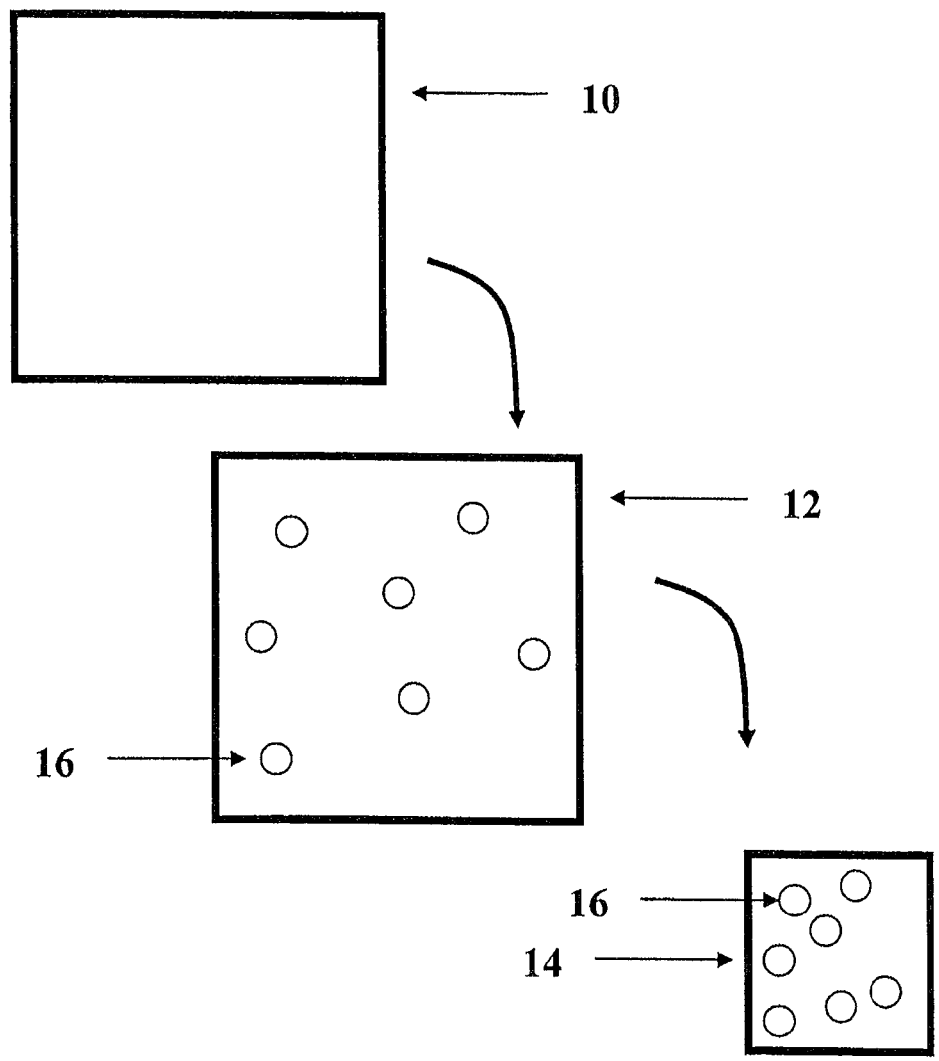
FIGS. 1 and 2 illustrate a compressed cloth having microencapsulated beads in accordance with various aspects of the present invention.

Referring now in detail to the drawings and, in particular, FIG. FIG. 1 illustrates one aspect of the present invention.

Article 10 is paper, a woven good or cloth. The article 10 can, for example, be made of rayon, but any compressible material can be used.

Microencapsulated beads or materials 16 are added to the article 10 by known techniques to form a new article 12. The microencapsulated beads 16 can be formed to be soluble in a liquid, such as water. In this case, the microencapsulated beads 16 will dissolve upon contact with the liquid and, upon being dissolved, will release the encapsulated material in the beads 16. The microencapsulated beads 16 can also be formed to break upon a pressure or friction being asserted on the beads 16. In this case, the beads 16 will break and release their contents upon the exertion of the pressure.

The article 12 having the microencapsulated beads can be compressed to a smaller size, such as the size of article 14, using any known technique, the techniques including but not limited to dehydration or submitting the article 14 to vacuum pressure. The size of the article 12 is usually small, such as the size of a coin or a button. Other sizes, however, can be used.

The materials in the microencapsulated beads 16 can include an antibiotic, a pharmaceutical, an alcohol, a fragrance, an oil, vitamin, a salt, a skin conditioner, a skin moisturizer, or combinations thereof. Other materials can include cleansers, polishes, anti itch materials and anti-inflammatory materials.

Any number of fragrances can be used. For example, aromatherapy fragrances thought to help calm people can be used. A bubble gum fragrance can also be used to provide a unique bubble bath for children.

Figure 2:
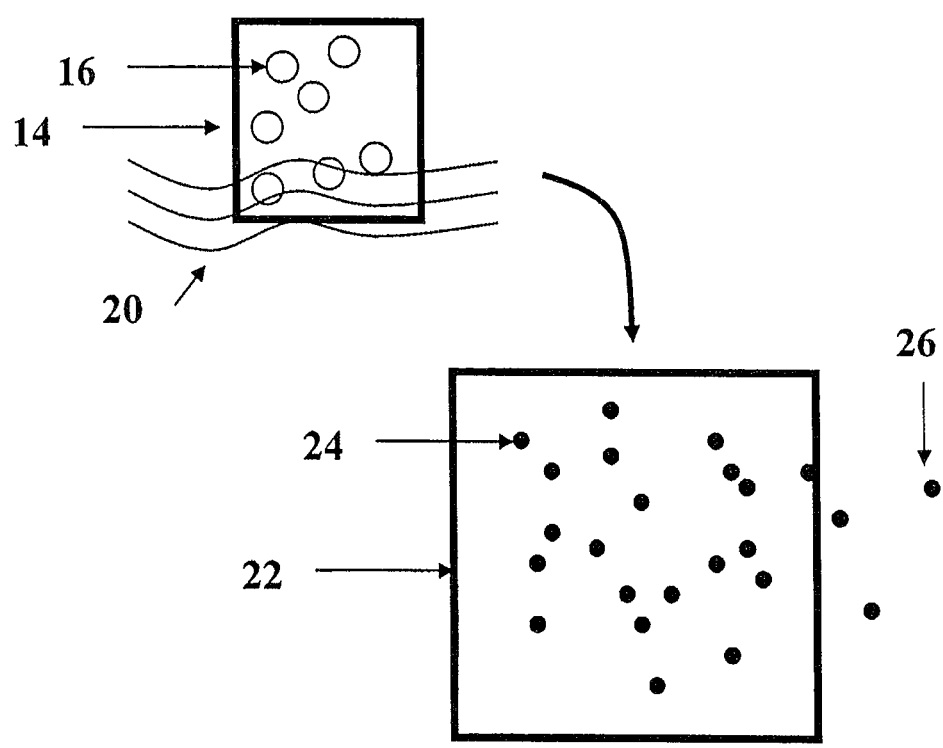

FIG. 2 illustrates the article 14 being exposed to a liquid 20. The liquid 20 can be any liquid that will de-compress the article 14. By way of example, the liquid could be water. The liquid 20, in this case, also preferably dissolves the microencapsulated beads 16 to release the contents of the beads.

The result of the application of liquid 20 is that the article 14 expands to the size of the article 22. The microencapsulated beads 16 have dissolved, releasing the contents 24 and 26. Generally, if the contents of the beads 16 were in liquid form, the contents 24 will stay on the article 22. If the contents of the beads 16 included fragrances, the contents 26 may leave the article 22.

In the case where the microencapsulated beads 16 are broken by friction, the application of the liquid 20 would not dissolve the beads 16. Instead, when the article 22 is rubbed on another article, such as a person's skin, the beads 16 are broken and the contents 24 and 26 are released.

The article 10 can be any compressible material that can be expanded.

Figure 3:
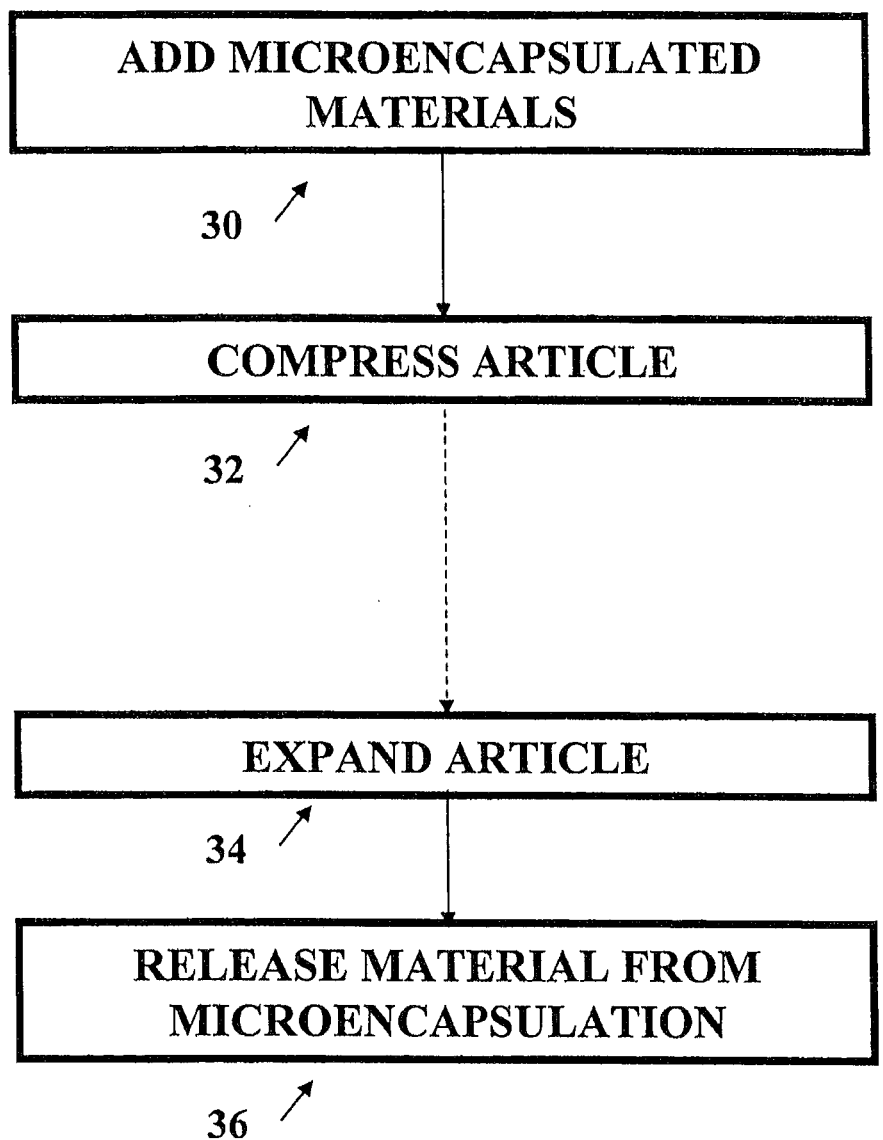
FIG. 3 illustrates a method in accordance with one aspect of the present invention.

FIG. 3 illustrates a method in accordance with one aspect of the present invention. In step 30, microencapsulated beads are added to an article. As stated before, the article can be cloth, a woven material, paper or any compressible material. In step 32, the article is compressed. The order of these two steps can be reversed.

In step 34, the article is expanded. In step 36, the contents of the microencapsulated beads 16 are released either as a result of contact with a liquid or as a result of friction or pressure.

The articles of the present invention can be used, by way of example only, to treat wounds, to provide therapy, such as aroma therapy or relaxation therapy, for bubble baths, for cleaning—both personal and for objects.

In accordance with another aspect of the present invention, the article 10 that is compressed can also be shaped. The article 10 can also have printed material on it. The shape of the article 10 and the printed material preferably have a relation to the article 10 and the material released by the microencapsulated beads 16. For example, if the article 10 is a wash cloth and the microencapsulated material is a bubble gum fragrance so that a child might enjoy a bath, the article 10 can be shaped like a cartoon character and a picture of the carton character can be printed on the article 10. For example, the article 10 could be shaped like Mickey Mouse and a picture of Mickey Mouse could be placed on the article 10.

Figure 4:
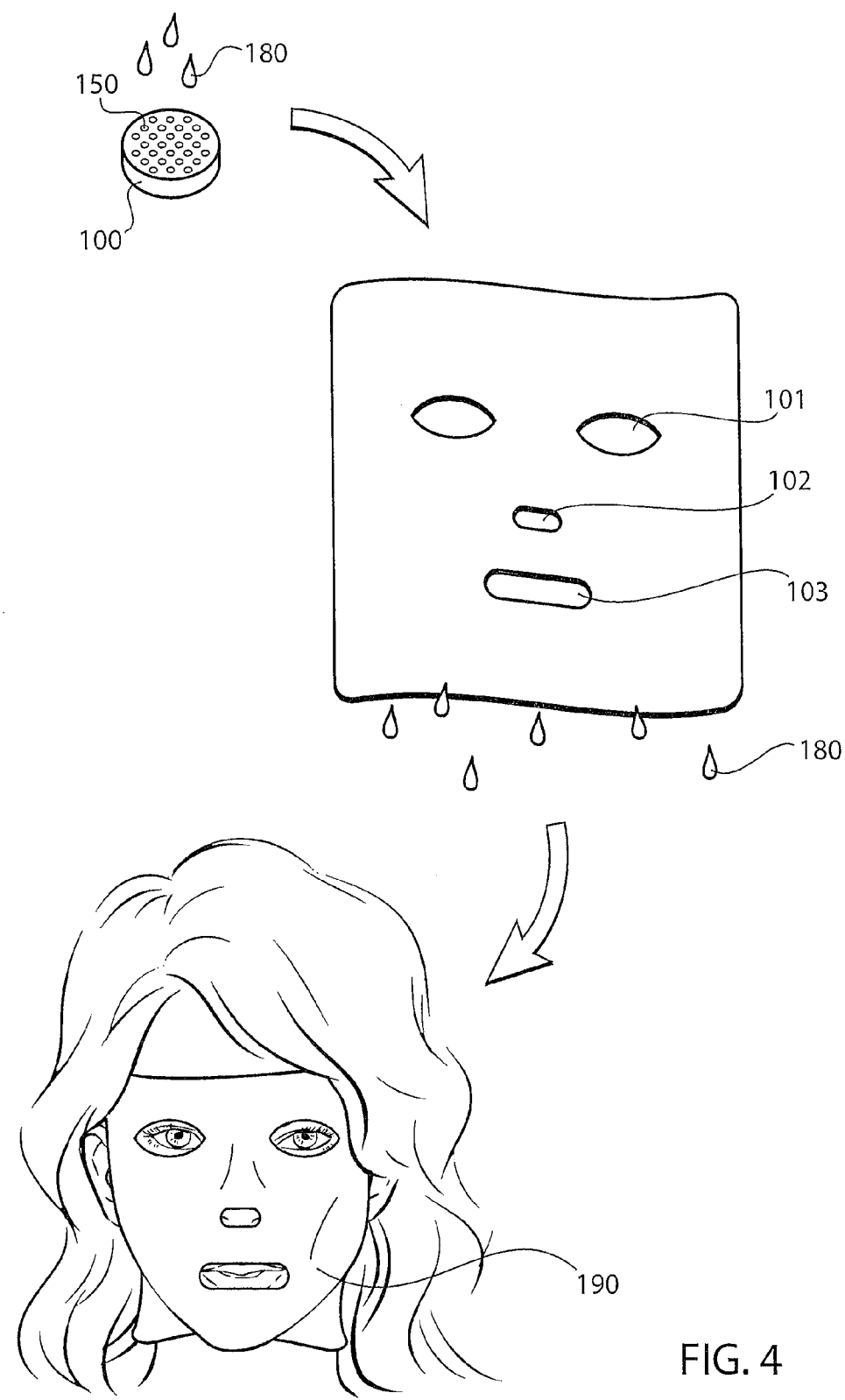
FIG. 4 illustrates the article in the form of a facial mask.

FIG. 4 shows another embodiment of the invention, in which article 100 is configured as a facial mask. Article 100 is compressed into a coin via vacuum compression, and expands into a facial mask shape, with cutouts 101, 102, 103 for the face, when contacted by liquid 180. Embedded into article 100 is a microencapsulated facial mask material 150 that is beneficial to the skin and hardens upon drying. Any suitable mask material could be used, such as clay, resin or other synthetic or organic materials. Application of article 100 to a face 190 allows article 100 to mold to the shape of the face and dry thereon, thus providing beneficial treatment to the skin.

Figure 5:
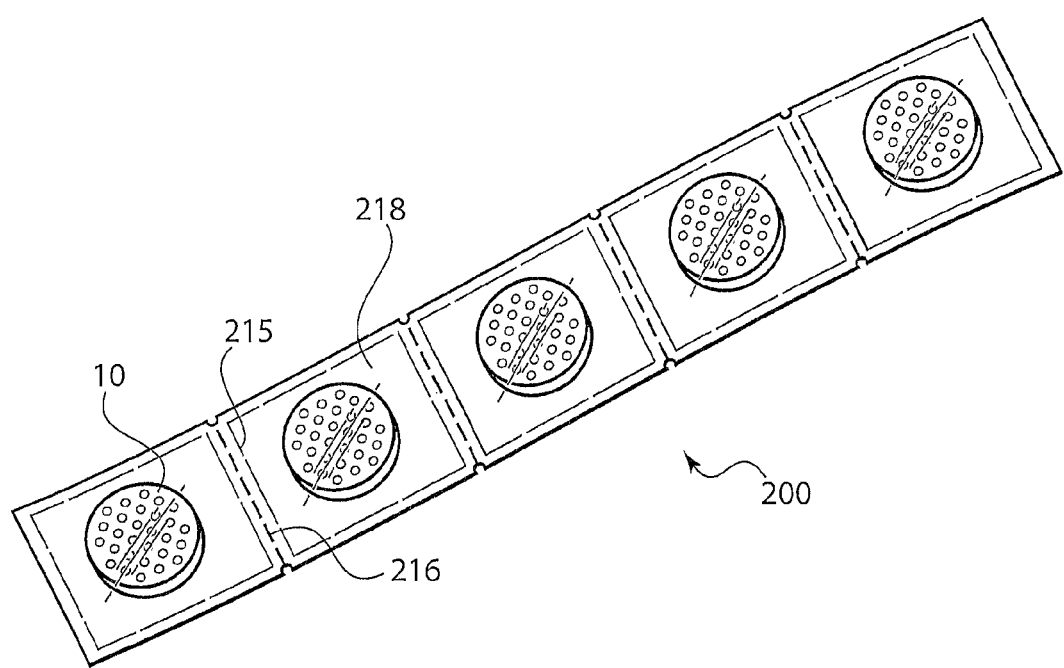
FIG. 5 illustrates several of the compressed articles in a strip of packaging.

FIG. 5 shows a strip 200 of compressed articles 10, which have been compressed into coin shape and are individually sealed in strip 200 in between sealed seams 215. Strip 200 can be decorated or colored to match the type of material embedded within article 10. In order to use an article 10, the portion of strip 200 adjacent article 10 is cut or ripped away from the rest of strip 200. Since each article 10 is individually sealed along seams 210, the remaining articles 10 stay sealed. Perforations 216 can be placed along seams 215 to make separation of each article 100 easier. A weakening line 218 can extend into the space between seams 215 to make tearing of the packaging easier when accessing article 100.

While there have been shown, described and pointed out fundamental novel features of the invention as applied to preferred embodiments thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. A compressed article of hygiene consisting of:
    a compressed cloth that has been compressed by dehydration or vacuum pressure into a coin shape and that is expandable upon contact with a liquid; and
    a plurality of microencapsulated beads containing a material, the plurality of microencapsulated beads being attached to the compressed cloth,
    so that, upon contact with water, expansion of the compressed cloth is unconstrained, and wherein the compressed cloth when expanded has a shape of a facial mask with openings for eye, nose and mouth, and wherein the material is a facial treatment material that hardens upon drying.

2. The article of claim 1, wherein the material is released from the beads upon expansion of the cloth in the liquid.

3. The article of claim 1, wherein the liquid comprises water.

4. The article of claim 1, wherein the material contains clay.

5. The article of claim 1, wherein the article is printed with a pattern or design.

6. A collection of compressed articles according to claim 1, wherein the articles are sealed in a strip of packaging such that each article is separable from the other articles without exposing the other articles to air.

7. The collection according to claim 6, wherein the strip contains sealed seams between the articles, and a perforation extends along each seam.

\* \* \* \* \*